United States Patent
DeTurk et al.

(10) Patent No.: US 10,271,988 B2
(45) Date of Patent: Apr. 30, 2019

(54) OPHTHALMIC SURGICAL INSTRUMENT WITH PRE-SET TIP-TO-SHELL ORIENTATION

(71) Applicant: Autocam Medical Devices, LLC, Kentwood, MI (US)

(72) Inventors: Neal Robert DeTurk, Hayward, CA (US); Wayne Frederick Schatz, San Jose, CA (US); Richard Lawrence Lucia, Livermore, CA (US); Andrew Robert Butron, San Jose, CA (US); Frank Tamayo Plascencia, Jr., San Leandro, CA (US); Terry Martin Yerka, Fremont, CA (US); Jose Eduardo Ameral, San Mateo, CA (US)

(73) Assignee: Autocam Medical Devices, LLC, Kentwood, MI (US)

( * ) Notice: Subject to any disclaimer, the term of this patent is extended or adjusted under 35 U.S.C. 154(b) by 262 days.

(21) Appl. No.: 15/071,386

(22) Filed: Mar. 16, 2016

(65) Prior Publication Data
US 2016/0242961 A1    Aug. 25, 2016

Related U.S. Application Data

(62) Division of application No. 13/757,983, filed on Feb. 4, 2013, now Pat. No. 9,320,648.
(Continued)

(51) Int. Cl.
*A61F 9/007*    (2006.01)
*H04R 31/00*    (2006.01)
(Continued)

(52) U.S. Cl.
CPC .......... *A61F 9/00745* (2013.01); *B21D 39/04* (2013.01); *B23K 26/206* (2013.01);
(Continued)

(58) Field of Classification Search
CPC ............. A61F 9/00745; A61F 9/00736; A61B 17/20068; A61B 2017/320084; A61M 1/0058; A61C 17/3409
See application file for complete search history.

(56) References Cited

U.S. PATENT DOCUMENTS

| 4,406,284 A | 9/1983 | Banko |
| 4,562,838 A | 1/1986 | Walker |

(Continued)

*Primary Examiner* — Rebecca E Eisenberg
*Assistant Examiner* — John A Doubrava
(74) *Attorney, Agent, or Firm* — Price Heneveld LLP

(57) ABSTRACT

An ophthalmic surgical instrument comprises a multi-diameter shaft, a horn fixedly threaded into the shaft, a surgical tip for ophthalmic surgery including a tip end and threadably engaging the horn opposite the shaft, and a plug on the shaft. Weld material holds the plug on the shaft in a selected angular and longitudinal position with an angle-locating recess on the plug's circumference having a predetermined angular clocked relation to a face direction of the tip end. The plug's recess engages an irrigation tube on a subassembled handle with shell and irrigation tube, such that the subassembled handle has a known clocked position relative to the tip end of the tip, thus facilitating use by a surgeon. A related method is also disclosed and claimed.

7 Claims, 11 Drawing Sheets

Related U.S. Application Data

(60) Provisional application No. 61/709,540, filed on Oct. 4, 2012, provisional application No. 61/709,547, filed on Oct. 4, 2012, provisional application No. 61/709,568, filed on Oct. 4, 2012.

(51) Int. Cl.
  *B21D 39/04* (2006.01)
  *B23K 26/20* (2014.01)
  *A61M 1/00* (2006.01)

(52) U.S. Cl.
  CPC ........ *H04R 31/00* (2013.01); *A61B 2217/005* (2013.01); *A61B 2217/007* (2013.01); *A61M 1/008* (2013.01); *A61M 1/0064* (2013.01); *Y10T 29/49005* (2015.01); *Y10T 29/49968* (2015.01)

(56) References Cited

U.S. PATENT DOCUMENTS

| | | | |
|---|---|---|---|
| 4,643,717 A | 2/1987 | Cook et al. | |
| 4,741,731 A | 5/1988 | Starck et al. | |
| 4,869,715 A | 9/1989 | Sherburne | |
| 4,989,583 A | 2/1991 | Hood | |
| 5,151,083 A | 9/1992 | Pichler | |
| 5,151,084 A | 9/1992 | Khek | |
| 5,162,044 A | 11/1992 | Gahn et al. | |
| 5,178,605 A | 1/1993 | Imonti | |
| 5,199,943 A | 4/1993 | Wypych | |
| 5,217,465 A | 6/1993 | Steppe | |
| D351,227 S | 10/1994 | Patton et al. | |
| 5,359,996 A | 11/1994 | Hood | |
| 5,382,162 A | 1/1995 | Sharp | |
| 5,413,556 A | 5/1995 | Whittingham | |
| 5,486,162 A | 1/1996 | Brumbach | |
| 5,580,347 A | 12/1996 | Reimels | |
| D388,170 S | 12/1997 | Sjostrom | |
| 5,722,945 A | 3/1998 | Anis et al. | |
| 5,843,109 A | 12/1998 | Mehta et al. | |
| 5,957,881 A | 9/1999 | Peters et al. | |
| 5,984,904 A | 11/1999 | Steen et al. | |
| 6,080,128 A | 6/2000 | Sussmn et al. | |
| 6,179,805 B1 | 1/2001 | Sussman et al. | |
| D440,310 S | 4/2001 | Laks et al. | |
| 6,234,993 B1* | 5/2001 | Terpilowski | A61M 1/0084 604/35 |
| 6,241,700 B1 | 6/2001 | Leukanech | |
| 6,256,859 B1 | 7/2001 | Stoddard et al. | |
| 6,287,274 B1 | 9/2001 | Sussman et al. | |
| 6,398,759 B1 | 6/2002 | Sussman et al. | |
| 6,602,193 B2 | 8/2003 | Chon | |
| 6,623,500 B1 | 9/2003 | Cook et al. | |
| 6,654,999 B2 | 12/2003 | Stoddard et al. | |
| 6,852,092 B2 | 2/2005 | Kadziauskas et al. | |
| 6,860,868 B1 | 3/2005 | Sussman et al. | |
| 6,902,558 B2 | 6/2005 | Laks | |
| 7,645,256 B2 | 1/2010 | Boukhny et al. | |
| 7,651,490 B2 | 1/2010 | Boukhny et al. | |
| 8,147,508 B2* | 4/2012 | Madan | A61B 8/4455 606/169 |
| 8,202,288 B2 | 6/2012 | Adams et al. | |
| 8,943,634 B2* | 2/2015 | Sokol | A61C 17/3481 15/22.1 |
| 2005/0159758 A1 | 7/2005 | Laks | |
| 2008/0139994 A1 | 6/2008 | Mackool et al. | |
| 2008/0281253 A1* | 11/2008 | Injev | A61F 9/00745 604/22 |
| 2010/0004585 A1 | 1/2010 | Boukhny et al. | |
| 2010/0056986 A1 | 3/2010 | Allen et al. | |
| 2010/0094198 A1 | 4/2010 | Burgett | |
| 2010/0274242 A1* | 10/2010 | Greep | A61B 18/1477 606/41 |
| 2010/0324581 A1 | 12/2010 | Mackool et al. | |
| 2011/0092888 A1 | 4/2011 | Gerg | |

* cited by examiner

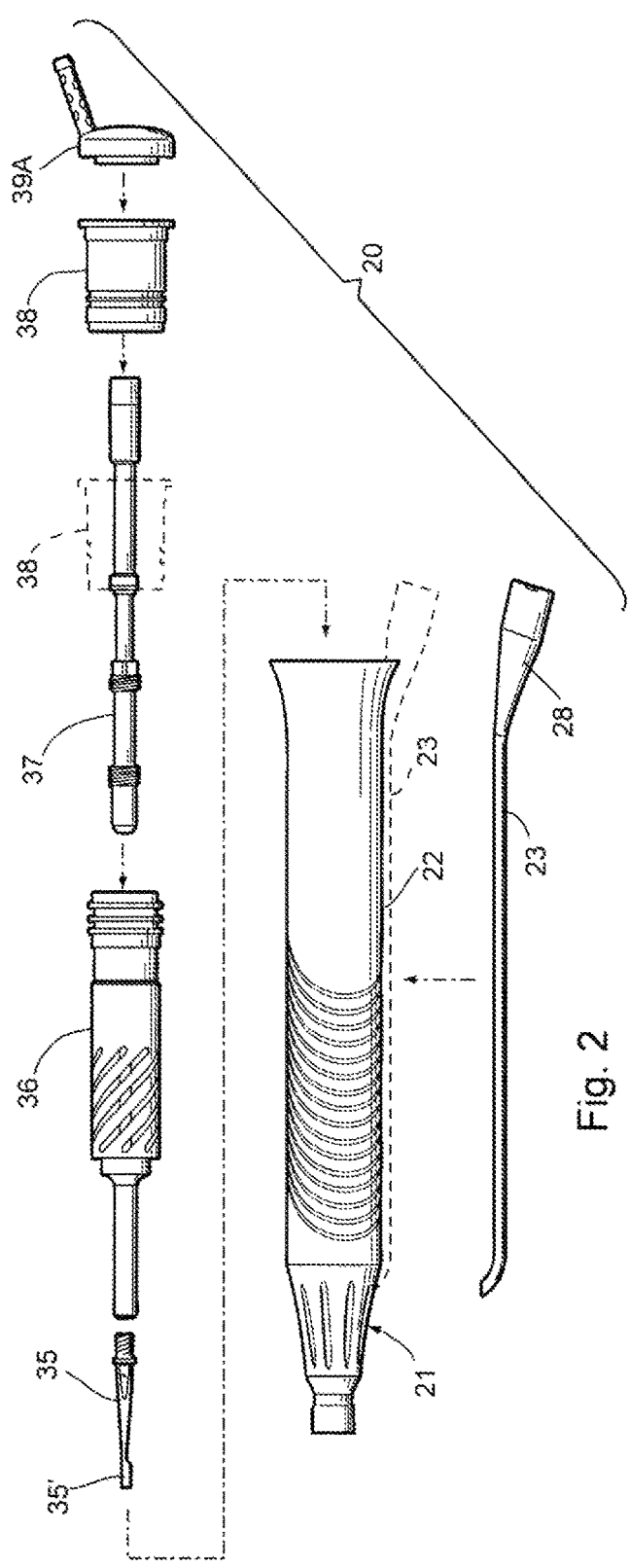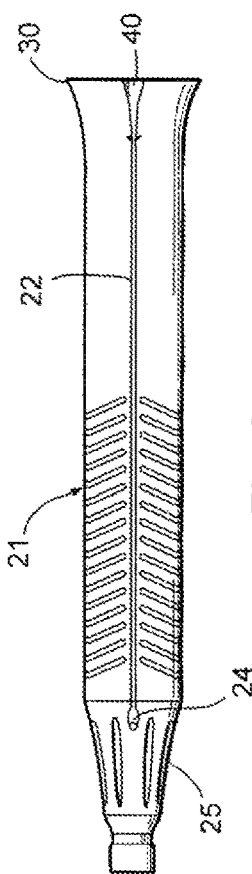

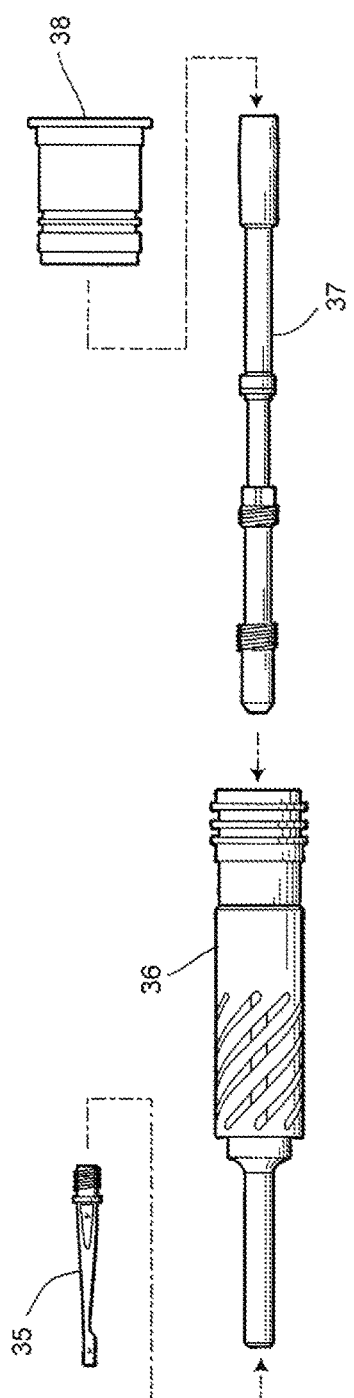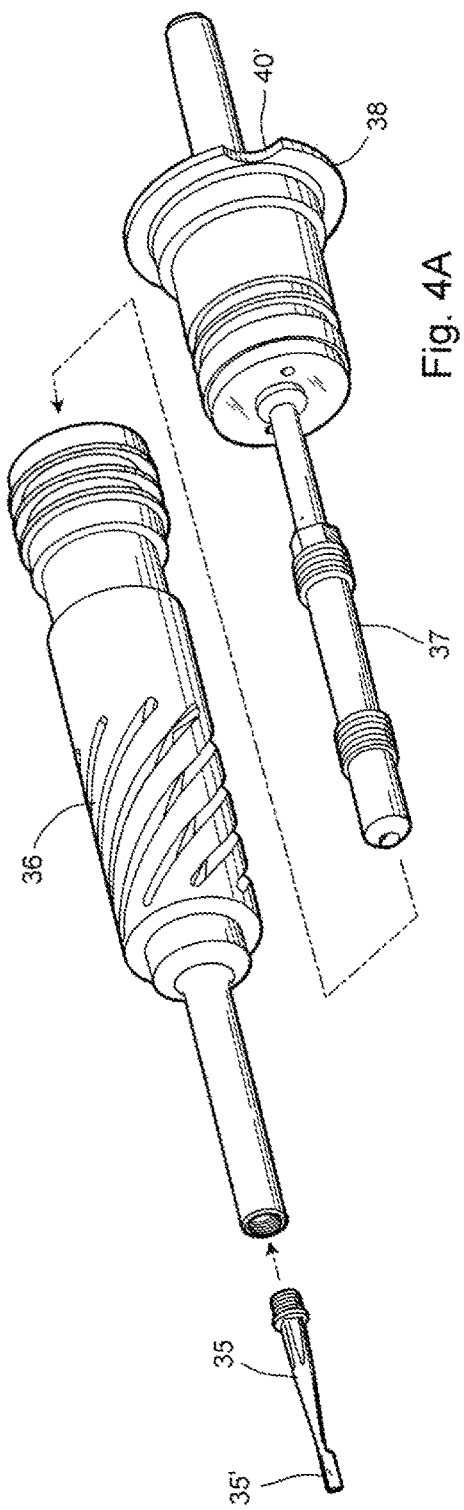

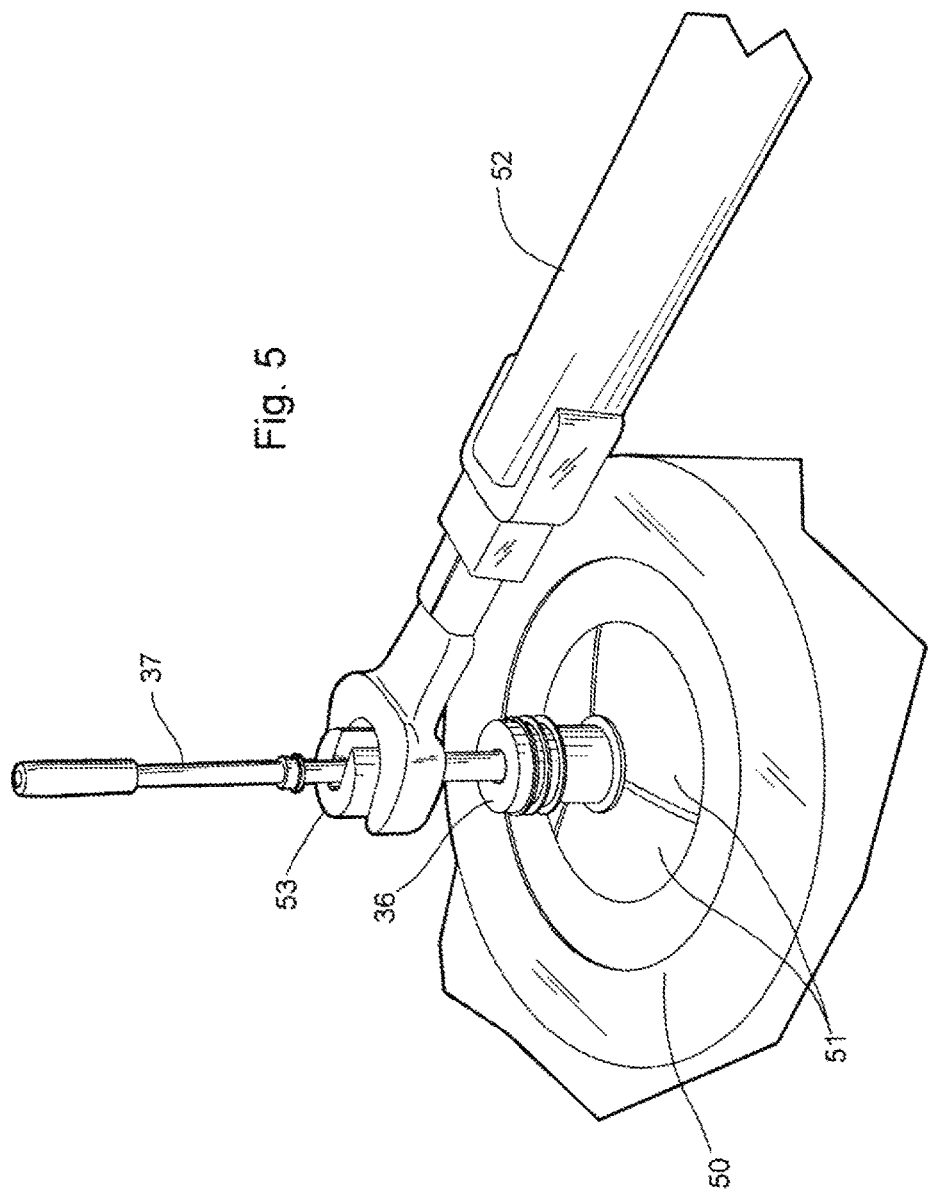

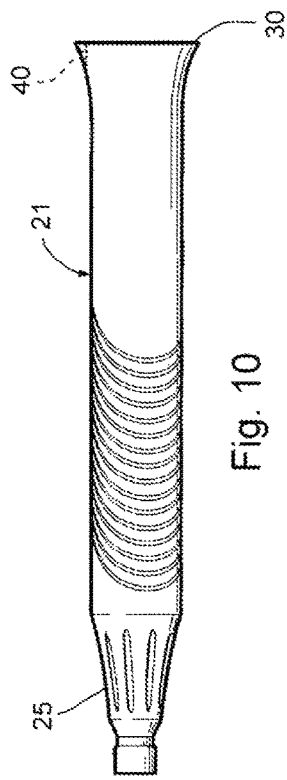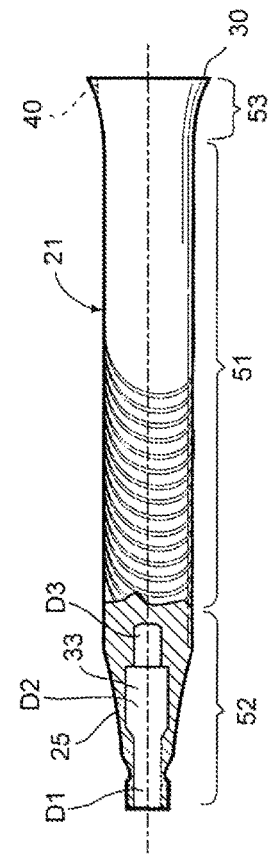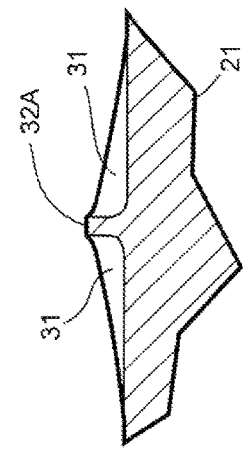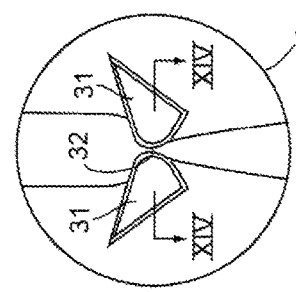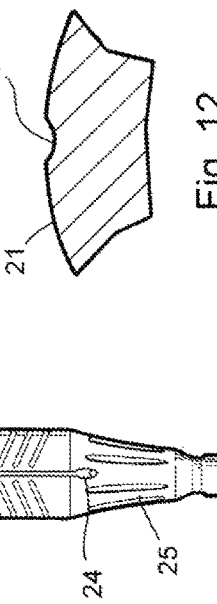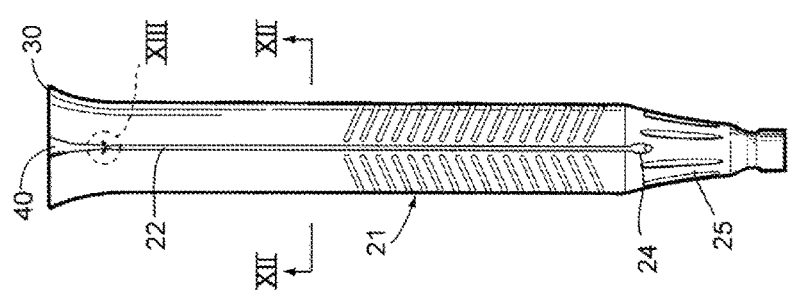

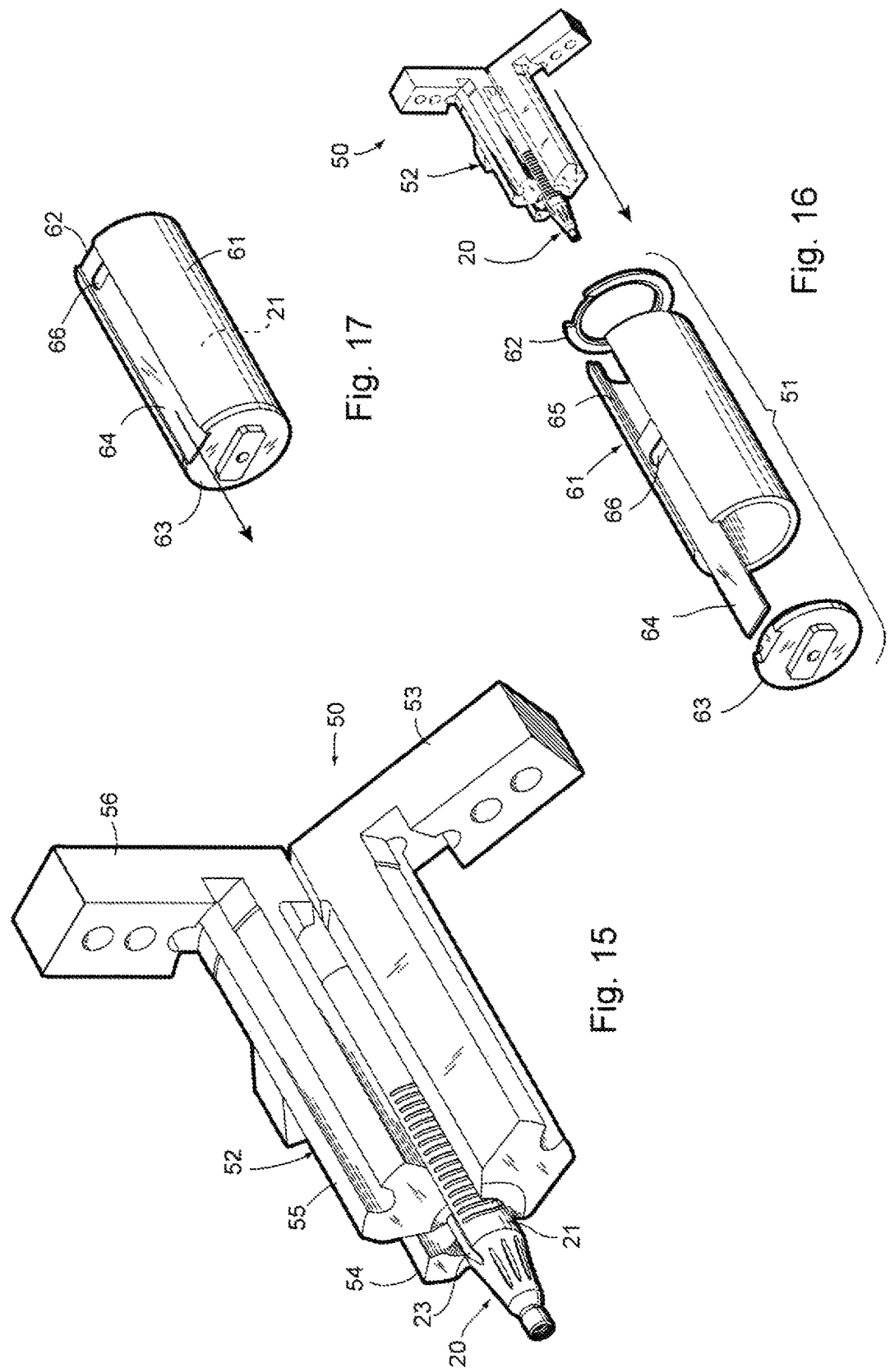

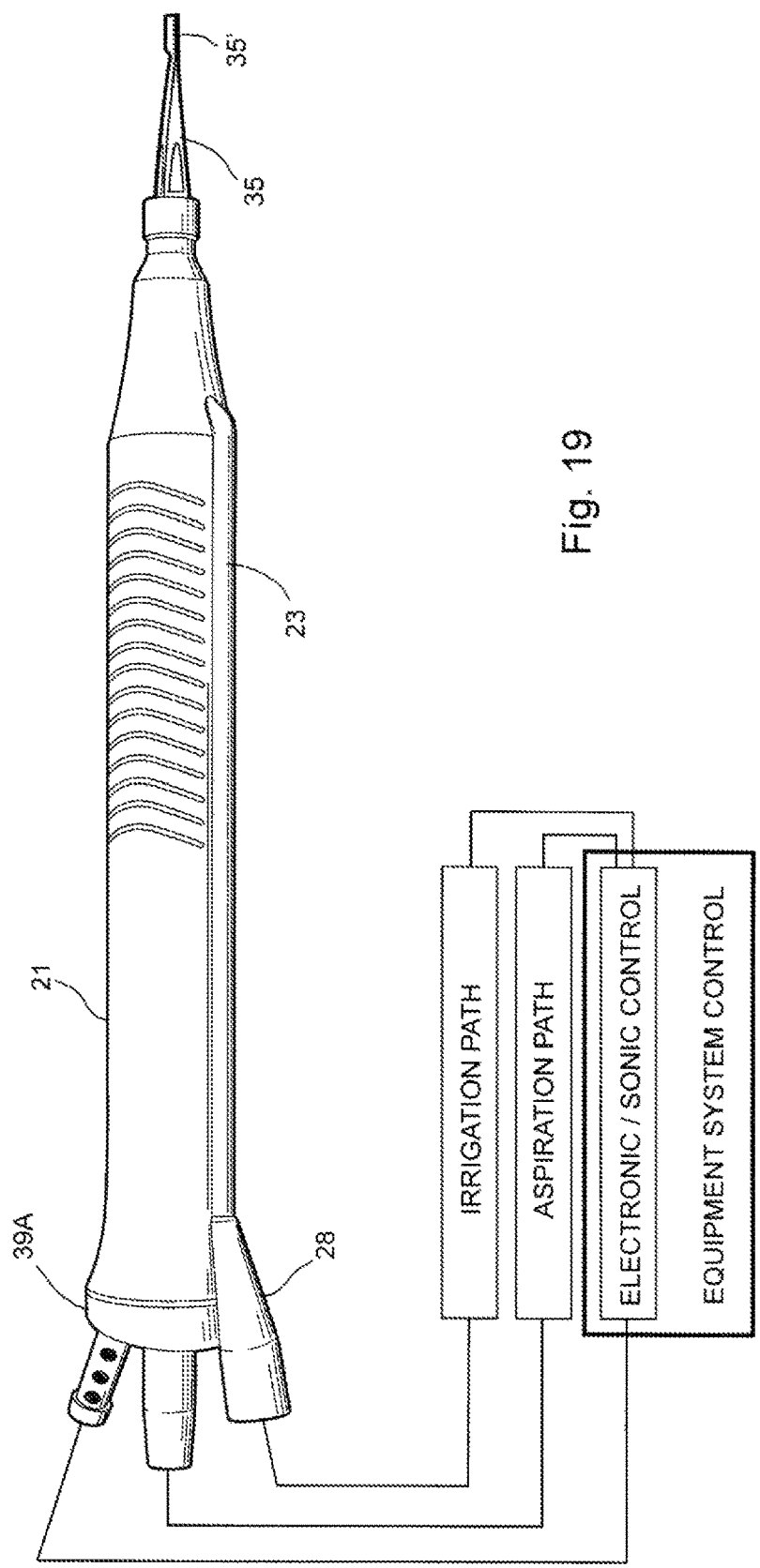

OPHTHALMIC SURGICAL INSTRUMENT WITH PRE-SET TIP-TO-SHELL ORIENTATION

CROSS-REFERENCE TO RELATED APPLICATION

This application is a divisional of U.S. patent application Ser. No. 13/757,983, filed on Feb. 4, 2013, now U.S. Pat. No. 9,320,648, issued on Apr. 26, 2016, entitled OPHTHALMIC SURGICAL INSTURMENT WITH PRE-SET TIP-TO-SHELL ORIENTATION which claims benefit under 35 USC § 119(e) of provisional application Ser. No. 61/709,540, filed Oct. 4, 2012, entitled OPHTHALMIC SURGICAL INSTRUMENT WITH WELDED IRRIGATION TUBE; provisional application Ser. No. 61/709,547, filed Oct. 4, 2012, entitled OPHTHALMIC SURGICAL INSTRUMENT WITH ONE-PIECE SHELL; and provisional application Ser. No. 61/709,568, filed Oct. 4, 2012, entitled OPHTHALMIC SURGICAL INSTRUMENT WITH PRE-SET TIP-TO-SHELL ORIENTATION, the entire contents of each of which are incorporated herein by reference.

BACKGROUND

The present invention relates to an ophthalmic surgical instrument with components facilitating clocked orientation of a surgical tip to its outer shell/handle, and components facilitating dimensionally-accurate manufacture including defect-free welding.

Ophthalmic surgical instruments are highly refined medical tools used in eye surgery, such as for cataract lens extraction. Such products are commercially manufactured and available, such as from Alcon company, including for example the Infinity® Vision System and/or Ozil® Vision System. It is important that the surgical instrument that contacts the patient and that is handled by the surgeon be of the highest quality, since the human eye is a delicate organ and the surgical procedure is very delicate. Therefore, reliability, durability, safety, ease of use, ease of sterilization, and numerous other aspects of the surgical instrument and related methods are very important. Also, physicians demand high quality and appealing aesthetics. At the same time, cost and manufacturability is important.

One tip used with hand-held ophthalmic surgical instruments is a replaceable tip, such as a phaco tip, with a straight end with beveled tip end, or a slightly bent/curved end with oriented tip end. Surgeons prefer that the bent/beveled end have a particular orientation relative to the handle when the surgeon picks up the instrument, so that the surgeon does not have to look to see the orientation of the bent/beveled end. In other words, surgeons want to intuitively known which way the bent/beveled end is "facing" when they pick up the instrument based on feel. The relative rotational orientation of parts is referred to herein as "clocking". Threaded connections provide an inconsistent angular rotational position (i.e. inconsistent "clocking"), particularly when torqued to a desired preload. Preloading is a requirement for these tips, since the instruments sonically vibrate the tips during use, and a significant torsional preload is required to prevent unacceptable risk of loosening during use. Depending on the design, the instrument may have multiple threaded connections for supporting the tip (e.g. a tip threaded into a horn, and also the horn threaded into a support shaft and/or to the handle/shell). Multiple threaded connections further amplify the problem of inconsistent "clocking" of the bent/beveled end to the instrument's handle/shell. Specifically, the combination of the threads, the preloads, and tolerance stack-up of the multiple components of the instruments makes it difficult to predict exactly what direction a bent/beveled end may face in a fully assembled instrument, thus resulting in an unacceptable number of bent/beveled tip ends being oriented outside a preferred angular range.

Some existing manufacturing processes and instrument designs attempt to deal with this clocking problem by replacing one or more of the threaded connection(s) with a press-fit arrangement, where the final clocked rotational position of the bent/beveled end (and/or of interconnected components affecting clocking of the bent/beveled end) is set by a press-fit process. However, press-fit assembly processes do not provide a strength, robustness, and durability of threaded connections. Further, the tips must be replaceable, which press-fit does not support. Still further, standard existing tips include threaded connections, so it is difficult to eliminate the use of threads, since the industry presently uses them. Nonetheless, it is potentially a significant advantage to provide features and/or characteristics that result in components pre-set at the factory to have a particular clocked orientation when assembled, such as at a supplier's site, rather than requiring this be done at the overall system equipment manufacturer/assembler.

The handset in the present ophthalmic surgical instrument includes several components made of titanium that are fixedly connected by welding. Though titanium is a preferred material for the present handset, titanium is difficult to weld in a defect-free manner. At the same time, surgical handsets must be made defect-free so as to avoid any cracks, crevices, or imperfections that might harbor germs and unwanted organics and contaminants. Notably, defects in handsets can cause an increase in sterilization time and/or frustrate optimal sterilization. Also, defective handsets can have appearance issues causing surgeons to object to or misinterpret the handset's quality.

In addition to high standards for defect-free handsets, ophthalmic handsets also have high standards for dimensional consistency and accuracy. Further, the handsets must be light in weight to facilitate easy and non-tiring use by the surgeon. Also, it is preferable that the handsets use a minimum of materials to reduce manufacturing cost. This leads to a dilemma where the handset's outer shell must preferably be thin-walled, yet thin walls can cause secondary problems. For example, some instrument designs require a thin-walled outer shell (such as an extruded thin-walled outer shell) welded to a machined tip. However, it is difficult to weld onto thin walls without distortion (due to the heat required for good welding, and/or issues related to non-uniform heating and later cooling), thus leading to welding defects and/or dimensional defects, especially near the weld area.

Thus, improvements are desired that positively affect each, any and all of the above items.

SUMMARY OF THE PRESENT INVENTION

In one aspect of the present invention, an internal subassembly for an ophthalmic surgical instrument comprises a multi-diameter shaft, a horn fixedly threaded into the shaft and that is constructed to provide sonic vibration energy to an end opposite the shaft, a surgical tip for ophthalmic surgery including a tip end at one end and a threaded end threadably engaging the horn opposite the shaft, the tip end defining a face direction, a plug on the shaft, and a flange with an angle-locating feature. The subassembly further includes weld material holding the plug on the shaft in a selected angular and longitudinal position with the angle-locating feature having a predetermined angular clocked relation to the face direction of the tip end.

In a narrower form, the angle-locating feature is a recess in an annular flange on the plug.

In another aspect of the present invention, an ophthalmic surgical instrument is provided that includes a second outer subassembly including a tubular shell and an irrigation tube attached to a side of the shell. The instrument includes the internal subassembly, as described above, assembled into the second outer subassembly with the recess engaging the irrigation tube on the annular flange of the plug, thus causing the tip end to be in a desired angular clocked position relative to the irrigation tube on the shell.

In another aspect of the present invention, a method of manufacturing an internal subassembly for an ophthalmic surgical instrument comprises providing a multi-diameter shaft, providing a horn adapted to generate sonic vibration energy, fixedly threading the horn and the shaft together, providing a surgical tip for ophthalmic surgery including a tip end at one end and a threaded end, threadably engaging the tip into the horn opposite the shaft, the tip end defining a face direction, providing a plug on the shaft and a flange with an angle-locating feature, and welding the plug to the shaft in a selected angular and longitudinal position with the angle-locating feature having a predetermined angular clocked relation to the face direction of the tip end.

In a narrower form, the angle-locating feature is a recess in an annular flange on the plug, and wherein the step of welding the plug includes engaging the recess with a feature in a welding holding fixture.

In a narrower form, the method includes providing a second outer subassembly having a tubular shell and an irrigation tube attached to a side of the shell, and including assembling the internal subassembly above into the second outer subassembly with the recess engaging the irrigation tube on the annular flange of the plug, thus causing the tip end to be in a desired angular clocked position relative to the irrigation tube on the shell.

In one aspect of the present invention, an ophthalmic surgical instrument comprises a combination including a tubular shell having a tip end portion and a tail end portion, and further having a channel extending from a hole into the tubular shell near the tip end portion and extending to the tail end portion; and an irrigation tube configured to matably engage the channel with a forward end shaped to dive into the hole and with a rear end extending at least to the tail end portion. The channel has a narrowed region shaped to facilitate initiation of a laser welding process by providing abutting contact between the tubular shell and irrigation tube that, in turn, provides access and point-focused heating from a laser beam welding operation, thereby facilitating heating and flowing of the material from the tubular shell into welded bonding contact with the irrigation tube with minimized physical and aesthetic defects and imperfections, yet without addition of separate welding material.

In a narrower form, the narrowed region includes deformed material of the shell that is deformed and pinched inwardly.

In another aspect of the present invention, a method of manufacturing an ophthalmic surgical instrument comprising steps of providing a tubular shell having a tip end portion and a tail end portion, and further having a channel extending from a hole into the tubular shell near the tip end portion and extending to the tail end portion, providing an irrigation tube shaped to matably engage the channel, and matably engaging the irrigation tube with the channel with a forward end of the tube positioned in the hole and a rear end of the tube extending to the tail end portion. The method further includes welding the tubular shell to the irrigation tube on both sides of the channel and for a length of the channel using material from the tubular shell and irrigation tube, the step of welding specifically not using separately added welding material, such as welding wire.

In a narrower form of the invention, the channel has a narrowed region shaped to abutting contact with the irrigation tube when the tube is placed in the channel, the narrowed region facilitating initiation of a laser welding process by providing access and point-focused heating from a laser beam welding operation, thereby facilitating heating and flowing of the material from the tubular shell into welded bonding contact with the irrigation tube with minimized physical and aesthetic defects and imperfections, yet without addition of separate welding material.

In still narrower form, the method includes deforming material of the shell to form the narrowed region by pinching and deforming material of the shell inwardly at the narrowed region.

In yet a narrower form, the step of pinching and deforming includes forming the narrowed region with two opposing embossments forming a butterfly-like shape with narrower portions near a center of the channel and wider portions on outboard edges of the narrower portions.

In one aspect of the present invention, an article for manufacturing an ophthalmic surgical instrument comprises a unitary metal rod blank made of continuous and contiguous material and that includes a unitary body and a tip end portion and a tail end portion. The tip end portion tapers from a diameter of the body to a narrowed tip dimension and is designed to support a sonically-vibrating tip extending longitudinally from the tip end portion. The tail end portion tapers from the diameter of the body to an increased tail dimension. The body and the tail end portion are a solid non-tubular metal rod of titanium material, but the tip end portion is machined to include a multi-diameter-defining internal cavity comprising a first section defining an end-adjacent first diameter, a second section defining a second diameter adjacent the first section, and a third section defining a third diameter adjacent the second section, with the second diameter being larger than the first and third diameters, such that the tip end portion facilitates and supports a sonically-vibrating tip. The metal rod blank is constructed to be machined to form a longitudinal bore through its length and also to be welded while maintaining a very accurate dimensional shape prior to being machined to form the longitudinal bore.

In a narrower aspect, the blank further has a hole in its tip end portion and a channel in an outer surface of at least the body and the tail end portion, the channel extending from the hole to the tail end portion.

In another aspect of the present invention, a method of manufacturing an ophthalmic surgical instrument comprises steps of providing a unitary tubular blank made of continuous and contiguous material and that includes a unitary body and a tip end portion and a tail end portion, with the body and the tail end portion being a solid non-tubular metal rod of titanium material, forming the tip end portion to form a taper from a diameter of the body to a narrowed tip dimension and so that the tip end portion is adapted to operably support a sonically-vibrating tip extending longitudinally from the tip end portion, and forming the tail end portion to form a taper from the diameter of the body to an increased tail dimension. The method further includes machining the tip end portion to include a multi-diameter-defining internal cavity comprising a first section defining an end-adjacent first diameter, a second section defining a second diameter adjacent the first section, and a third section defining a third diameter adjacent the second section, with the second diameter being larger than the first and third diameters, such that the tip facilitates and supports a sonically-vibrating tip end. The non-tubular metal rod is constructed to be machined to form a longitudinal bore through its length and also be welded while maintaining a very accurate dimensional shape.

In a narrower form, the method includes machining a longitudinal cavity through the rod, the longitudinal cavity including the internal cavity.

In a narrower form, the method includes forming a channel in an outside surface of the blank that extends from a hole in the tip end portion to the tail end portion.

In a narrower form, the method includes steps of providing an irrigation tube shaped to matably engage the channel, matably engaging the irrigation tube with the channel with a forward end of the tube positioned in the hole and a rear end of the tube extending to the tail end portion, and welding the tubular shell to the irrigation tube on both sides of the channel and for a length of the channel using material from the tubular shell and irrigation tube.

An object of the present invention is to provide an ophthalmic surgical instrument and method of manufacture where the instrument includes a tubular shell with channel and mating irrigation tube attached along a side of the shell, but where the tubular shell is initially made from a one-piece continuous and contiguous titanium metal rod machined at a tip end portion to include a multi-diameter cavity for supporting a sonically-vibrating tip. A remainder of the rod is not initially machined, which eliminates problems of alignment and dimensional distortion caused by secondary operations such as welding, but instead is machined later in the secondary processes, such as after welding. The present innovation eliminates the need to perfectly align and then weld a machined tip end to an end of a thin-walled tubular shell, thus avoiding considerable process control and quality issues.

These and other aspects, objects, and features of the present invention will be understood and appreciated by those skilled in the art upon studying the following specification, claims, and appended drawings.

BRIEF DESCRIPTION OF DRAWINGS

FIGS. 1-2 are perspective and exploded side views of an ophthalmic surgical instrument's handset with tubular outer shell and welded exterior irrigation tube and clocked internal components, embodying the present invention.

FIG. 3 is a side view of the tubular shell from FIG. 1, showing a side with the tube-receiving exterior channel for receiving the irrigation tube.

FIGS. 4 and 4A are exploded side and exploded perspective views like FIG. 2 but showing only the internal subassembly of the tip, the horn, the multi-diameter shaft, and the plug.

FIG. 5 is a perspective view showing assembly of the shaft to the horn from FIG. 4 using a torque wrench and fixture.

FIG. 9 is a partial cross-section taken along line IX-IX in FIG. 3.

FIGS. 10-11 are side views of a rod blank (i.e. rod) of unitary, continuous, and continuous titanium material (i.e. a rod of solid material) that is machined out to form the shell shown in FIGS. 1-3, FIG. 10 being a side view without cross-section, and FIG. 11 being a longitudinal cross-section through the tip end portion to show the internal multi-diameter machined cavity, the tip being machined prior to drilling out a remaining body to the opposite end of the rod blank.

FIG. 12 is a side view of the shell in FIG. 10 on a channel-side where the irrigation tube channel is formed.

FIG. 13 is an enlarged view of the circled area labeled XIII in FIG. 12.

FIG. 14 is a cross section taken along line XIV-XIV in FIG. 13.

FIG. 15 is a perspective view of a welding fixture including weld jaws for holding the irrigation tube in place on the outer shell when welding the irrigation tube to the shell.

FIGS. 16-17 are perspective exploded and perspective assembled views of a gas chamber for welding the shell and irrigation tube of FIG. 15 together; FIG. 16 showing a general shape and position of the gas chamber relative to the jaws in the fixture from FIG. 15.

FIGS. 18-19 are exploded and assembled views of an ophthalmic surgical instrument (less electronics and utility wiring/tubing), the outer piece including a shell and weld-attached irrigation tube like that shown in FIG. 2, FIG. 19 also showing the system controls and fluid paths.

DETAILED DESCRIPTION OF PREFERRED EMBODIMENTS

Figure 1:
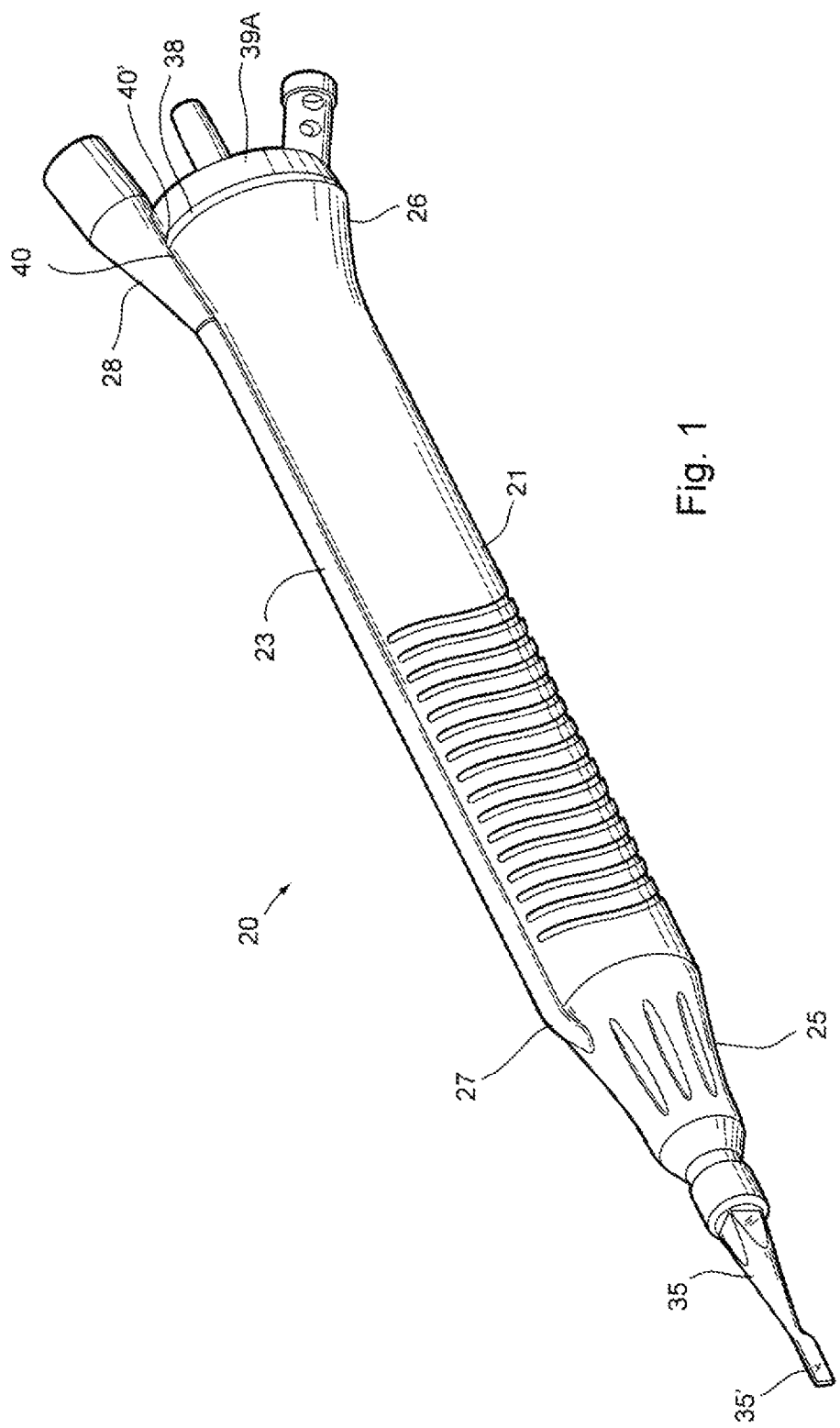

As noted above, ophthalmic surgical instruments and systems are generally known by persons skilled in the art; therefore, a detailed description of their function, use during surgery, electronic internal components, external controls, and general system is not necessary for an understanding of the present invention. Accordingly, the present disclosure focuses on the present pre-clocked innovative assembly of an internal subassembly (with tip, horn, multi-diameter shaft, and plug) mated with an external subassembly (with tubular shell and irrigation tube), including features causing accurate clocking upon assembly, secure mating and defect-free welding interconnection, and including weld-facilitating features, fixturing and welding processes associated therewith.

More specifically, an ophthalmic surgical instrument is provided that includes a tubular shell with external channel and mating irrigation tube attached along a side of the shell. Notably, the present tubular shell is made from a one-piece continuous and contiguous titanium metal rod blank machined at its tip end portion to include a multi-diameter cavity for supporting a sonically-vibratable tip. A remainder of the rod is not initially machined, which eliminates problems of alignment and dimensional distortion caused by weld-related secondary operations. The present innovation eliminates the need to perfectly align and then weld a machined tip to an end of a thin-walled tubular shell, thus avoiding considerable process control and quality issues. After the tip end portion is machined and formed (externally and internally), a thru-bore is drilled through a remainder of the rod blank to form the remaining portion of the rod blank into a thin-walled outer shell useful for operatively holding an internal assembly (i.e. the internal subassembly including the tip, horn, multi-diameter shaft, and plug, described below).

The present apparatus 20 (also called "an ophthalmic surgical instrument") (FIGS. 1-3) includes a first (outer) subassembly including a tubular shell 21 with channel 22 and mating irrigation tube 23. The channel 22 is formed in an outer surface of the shell 21, and extends from an angled radial hole 24 near a tip end 25 of the tubular shell 21 to a tail end 26. The irrigation tube 23 fits matably in the channel 22, and includes a bent forward end 27 that fits into the hole 24, and includes a rear end adapter 28 on the tube 23 extending past an open notch 40 in the tail end of the channel 22 formed by an annular flange 30 of the tubular shell 21. The combination of the tubular shell 21 and irrigation tube 23 form a handle that can be easily and comfortably grasped by a surgeon, with the surgeon easily recognizing the orientation of the handle by feel due to the clocked (rotational position) of the tube 23 and shell 21 to the tip 35.

The present apparatus 20 (FIGS. 2, 4, 4A) includes a second (internal) subassembly including a tip 35, a horn 36, a shaft 37, and a plug 38. It is noted that various tips are commercially available and can be used with the present innovation. The illustrated tip 35 includes an enlarged slightly-curved and/or beveled sharp tip end 35' on its outer end for cutting (during a surgical procedure), and includes threads on its inner end for threaded secure connection to the tip end portion of the horn 36. The horn 36 is designed to sonically vibrate and precisely move the tip end 35' on the end of the tip 35 for optimal cutting and surgical application. The multi-diameter shaft 37 (also sometimes called a "bolt") is threaded into a tail end of the horn 36. The plug 38 is rotatably positioned on the shaft 37 and includes an outwardly-extending annular flange with a notch 40' along its perimeter. The notch 40' is designed to receive and matingly engage the adapter 28 of the irrigation tube 23 (on the first outer subassembly) when the second internal subassembly is assembled into the first outer subassembly, as described below. Also, the plug 38 has a notch 40' that aligns with and generally matches notch 40'.

FIG. 5 shows threaded assembly of the shaft 37 to the horn 36, and illustrates that the horn 36 is clamped and held by a collet 50 with jaws 51 while the shaft 37 is screwed into the horn 36 and then tightened to the specified torque using a torque wrench 52 and torque wrench adapter 53 (the adapter 53 protecting the hex on the shaft 37). The tip 35 is screwed into the end of the horn 36 with a predetermined torsional pretension to prevent accidental release when being vibrated during use. At this point, the horn 36 and the shaft 37 are interlocked by a strong threaded union. The tip 35 is similarly threaded into a tip end of the horn 36 with a threaded connection, including a significant torsional pretension as required by the design.

A fixture 45 (FIGS. 6-7) includes a body 46 that holds the second (internal) subassembly in a particular known rotational orientation relative to the plug 38 while the plug 38 is welded in position on the shaft 37. The fixture 45 includes an adapter-simulating feature 47 (i.e. similar in external shape to the adapter 28 on the irrigation tube 23) that keeps the plug 38 in proper clocked orientation during the welding process by engaging notches 40 and 40' (FIGS. 3 and 4A). Notably, the illustrated weld can be done without addition of separate welding material, as described below. Restated, the present innovative process does not require the use a welding wire or external welding material.

Figure 6:
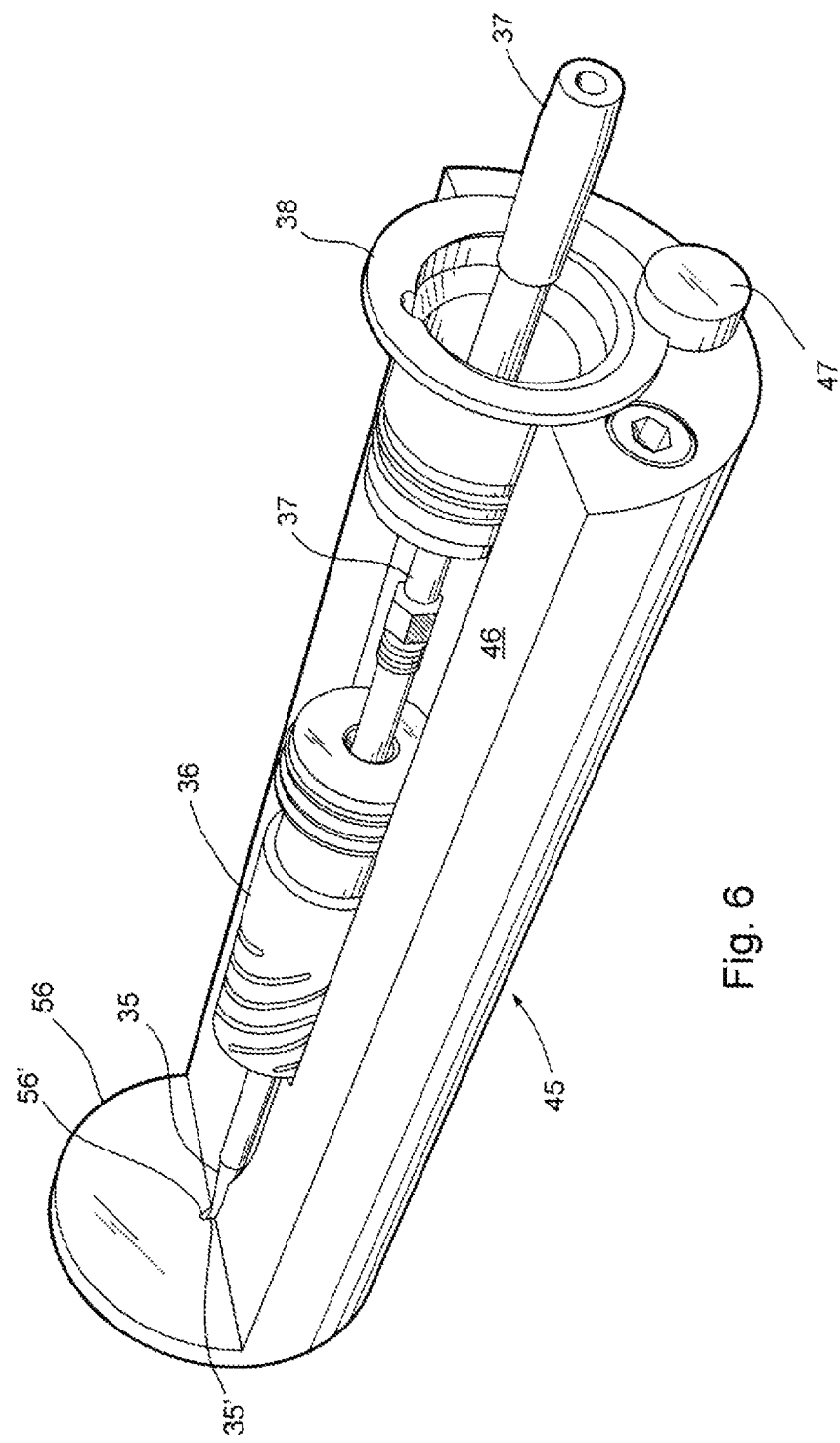
FIGS. 6-7 are perspective and side views showing components from FIG. 5 threaded together with a tip to form a first subassembly (i.e. a preassembled tip and horn and shaft) and a plug rotatably supported on the first subassembly, all positioned in a welding fixture for holding the first subassembly (and the tip) in a specific clocked position relative to a notch in the plug, the fixture facilitating welding of the plug to the first subassembly in known clocked orientation.

FIG. 6 shows the first (internal) subassembly (i.e. a threadably-engaged preassembled tip 35 and horn 36 and shaft 37 from FIG. 5) positioned in the fixture 45. The plug 38 is slipped onto the shaft 37 and rotatably supported on the shaft 37 of the first subassembly by the weld orientation fixture 45. The welding fixture 45 includes an end piece 56 with a fixture orientation pin (not specifically shown) at location 56' that engages a side edges (or flat side) of the tip end 35' on the tip 35 to orient the first subassembly in a specific clocked (rotational) position. As illustrated, the protruding feature 47 also engages the notch 40' in the plug 38, thus orienting the notch 40' relative to an orientation of the tip end 35' (i.e. "clocking" the tip 35 to the plug 38, such as to a predetermined angular specification such as at 180 degrees, such as with +/−5 degrees tolerance, or potentially a tighter tolerance such as 2½ degrees). The plug 38 is then welded to the shaft 37, fixing its rotational orientation. Notably, as long as replacement tips 35 are purchased from the same supplier, our testing shows that the threaded end of the common-supplier tips 35 is consistent enough to provide good and accurate clocking when an original tip 35 is replaced with a replacement tip 35, such as within +/−5 degrees, or even within +/−2-½ degrees. However, the threaded connection between the horn 36 and shaft 37 is less consistent, and further there is a tapered interfacing surface that further renders the connection to have an inconsistent clocked position upon connection. The present innovation solves that problem.

Figure 7:
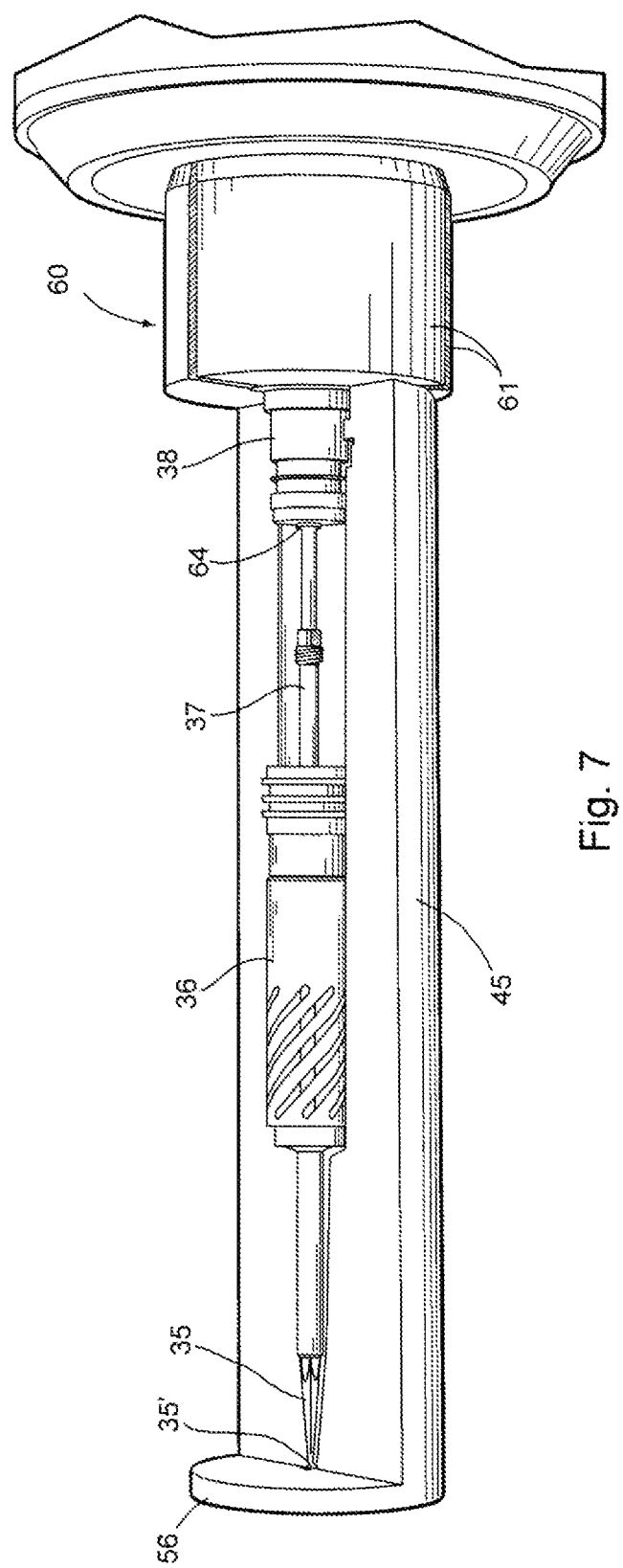

FIG. 7 illustrates an additional component of the fixture 45, which includes a collet/clamp 60 with jaws 61 for gripping the plug 38 and for holding the specific angular clocked position relative to a direction of the tip end 35'. It is contemplated that the collet/clamp 60 could also be constructed to rotate the plug 38 to a desired orientation. The fixture 45/60 then holds the plug 38 for initial welding at location 64.

Figure 8:
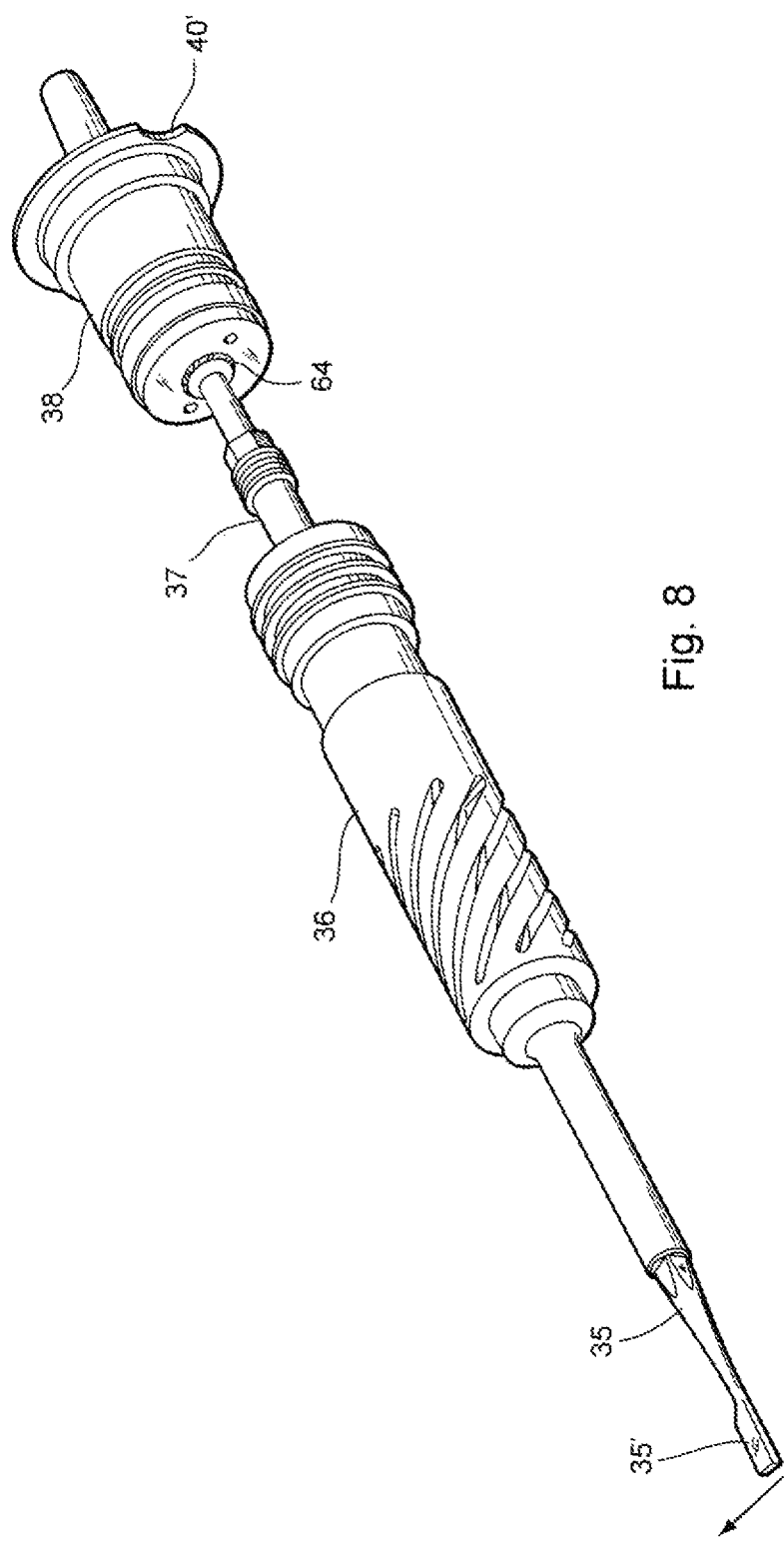
FIG. 8 is a perspective photograph showing a completed welded assembly of the first subassembly from FIG. 6 (i.e. the tip, horn, shaft, and plug) with the plug welded to the shaft.

FIG. 8 illustrates the first (internal) subassembly as welded and interconnected, including the tip 35 fixedly threaded to the horn 36, the horn 36 fixedly threaded to the shaft 37, and the plug 38 fixedly welded to the shaft 37, all with an angular direction of the tip end 35' and of the notch 40' being within a angular tolerance such as 180 degrees, +/−5 degrees (or a narrower range such as +/−2½ degrees).

The controls for the welding operation may be varied as needed for a particular welding operation. It is contemplated that the weld can be done with or without welding wire. In the present innovation, the following parameters were used in welding the illustrated prototype with no weld wire and no added weld material being used. Notably, a skilled artisan will recognize that the laser power and parameters can be adjusted during the welding process for optimal results for a particular application:

EXAMPLE: Resonator set-up: Beam expander—2.0, front mirror—150 mm, aperture—5.8 mm to 4.0, rear mirror—150 mm, and rear mirror type flat; Laser Work Parameter Setting: pulseform—N/A, frequency 15 Hz to 40 Hz, pulse duration—4.0 ms to 0.5 ms, volts—241 v to 257 v, energy—3.0 is min to 0.1 is min, E-control—off, beam expander—216, burst number N/A, ramp number 10, ramp power—N/A, ramp pulse—0.1 ms, gas advance—0.1, delay—0.1, 2-cavities—sim; and Peripherals: nozzle—graphite, nozzle length—0.600" to 0.500", assit gas type— argon, assit gas flow—10 cfh, final focus setting 1.0 mm to 4.0 mm, Z height—1.028" to 1.150", and work coordinate—G54.

As noted above, the present innovation also includes making the entire shell 21 out of a one-piece titanium-metal rod blank. This is done to eliminate several problems. For example, the present innovation avoids alignment and welding problems associated with welding a machined tip onto the thin-walled extruded tubular shell (e.g. problems including mechanical alignment, distortion from non-uniform heat of welding and later cooling, and deformation that occurs in secondary operations necessary to attach a machined tip to a front end of a hollow tubular shell). The method of manufacturing the ophthalmic surgical instrument 20 comprises steps of providing a unitary one-piece solid rod blank (also called a "rod" herein) (FIGS. 10-14) made of continuous and contiguous (non-welded) titanium material and that includes a unitary non-tubular body 51 and a tip end portion 52 (which later becomes tip end portion 25) and a tail end portion 53 (which later becomes tail end portion 26). The tip end portion 53 is machined to define a multi-diameter internal cavity 33, but the body 51 and the tail end portion 53 are temporarily left as a non-tubular solid mass of titanium material. The method includes forming (e.g. machining and/or forming) an outer surface of the tip end portion 52 to form a configured taper from a diameter of the body 51 to a narrowed tip dimension and so that the tip end portion 52 is adapted to operably support a sonically-vibrating beveled tip 35 with beveled end surface extending longitudinally from the tip end portion 52. Also, shape and surface texture of the taper in tip end portion 52 and body 51 includes grooves that provide a finger grip for a surgeon's fingers. The method includes forming the tail end portion 53 to form a flared taper extending from the diameter of the body 51 to an increased tail dimension. Also, the method includes machining the tip end portion 52 to include the multi-diameter-defining internal cavity 33 comprising a first section defining an end-adjacent first diameter D1, a second section defining a second diameter D2 adjacent the first section, and a third section defining a third diameter D3 adjacent the second section, with the second diameter D2 being larger than the first and third diameters D1 and D3. The tip end portion 52 is constructed and adapted to clearly receive and support the sonically-vibratable tip 34.

The non-tubular body 51 and tail end portion 53 are believed to be novel and unobvious since they are initially a non-tubular solid mass of material. By being a solid mass, they can be welded on more easily without dimensional distortion. Also, they are constructed to be accurately machined later in the manufacturing process to form a very accurate and centered longitudinal bore (i.e. very accurate thin wall thickness, such as a thickness of less than 1 mm in some places) through the length of the shell 21. The solid mass also allows the part to be welded on while maintaining a very accurate dimensional shape. Notably, after a welding operation, the shell 21 is annealed to improve dimensional stability and accuracy during later secondary processing.

As noted above, the channel 22 is formed in an outer surface of the shell 21, and extends from a hole 24 near a tip end portion 25 and to a tail end portion 26 (FIG. 1). The irrigation tube 23 (FIG. 2) is pre-formed to fit matably in the channel 22, with its bent forward end 27 (FIG. 1) fitting into the hole 24, and with a rear end adapter 28 (FIG. 2) on the tube 23 extending past an open notch 40 of the channel 22 formed by an annular flange 30 of the tubular shell 21. The channel 22 has an embossed narrowed region 32 (FIGS. 12-14) with protruding ridge 32A. The ridge 32A is configured to abut the tube 23 when first fixtured together. The embossed area around the narrowed region 32 is shaped somewhat like a butterfly and, when formed, causes the ridge 32A to slightly rise above the channel 22. As will be recognized by a skilled artisan in welding, this ridge 32A facilitates initiation of a laser welding process by providing good abutting contact between the tubular shell 21 and irrigation tube 23 at ridge 32A, both in terms of providing access and also providing point-focused heating, such as for a laser beam welding operation. Specifically, it facilitates heating and flowing of the material from the tubular shell 21 into welded bonding contact with the irrigation tube 23 with minimized physical and aesthetic defects and imperfections, yet without the need for addition of separate welding material. Notably, the embossment feature (i.e. ridge 32A) is consumed and unidentifiable after welding.

The method of manufacturing the ophthalmic surgical instrument 20 comprises steps of matably engaging the irrigation tube 23 with the channel 22 (FIG. 2) with a bent forward end 27 (FIG. 1) of the tube 23 positioned in the hole 24 and a rear end adapter 28 (FIG. 2) of the tube 23 extending to the tail end portion 26 (FIG. 1). The method further includes laser beam welding the tubular shell 21 to the irrigation tube 23 on both sides of the channel 22 with the welding extending a length of the channel 22, the weld material being from the tubular shell 21 and/or the irrigation tube 23. Notably, the illustrated step of welding does not use separately added welding material, such as welding wire. Notably, even though the present innovation uses zero external weld material and laser welding, it is contemplated that a scope of the present innovation includes supplying added welding material and/or using a different welding process.

Notably, the irrigation tube must be fully "sealed" after welding. In other words, when fluid in the irrigation tube fills up the nosecone portion of the shell, no fluid can leak back to the outside of the hand piece. The illustrated "butterfly wing" design is believed to greatly assist in creating a tight and good seal during the welding process. This is believed to be in part because the thinning at a specific point allows the manufacturer to use the laser and fixturing to "pinch" the material together, resulting in an improved and better and more consistent seal.

Welding titanium material is difficult, and requires that the area to be welded be oxygen-free during the welding operation. The fixture 50 (FIG. 15) and gas chamber 51 (FIGS. 16-17) are designed to facilitate the present welding operation, including making the operation more efficient while using less wasted oxygen-eliminating gas during the welding operation. The fixture 50 (FIG. 15) includes multiple L-shaped weld jaws 52-54 (three being illustrated). One jaw 52 is designed to abut the tube 23 and hold the irrigation tube 23 in the channel 22 (FIG. 9) and against the shell 21. The other two jaws 53-54 are radially spaced to oppose the jaw 52 and securely hold the assembly (including the shell 21) during the welding process. The L-shaped jaws 52-54 each include a shell-engaging longitudinally-protruding arm 55 for engaging the shell 21/tube 23, and include a radially-extending base-supported arm 56 adjustably supported to move the shell-engaging arm 55 into and out of fixturing clamped engagement with the shell 21 and tube 23.

The gas chamber 51 (FIG. 16) includes a main body 61, an aperture end cap 62 (for receiving the shell-engaging arms 55 of the jaws 52-54), a closed end cap 63, and a cover slide 64. The main body 61 includes an open side covered by the cover slide 64, and the cover slide 64 is slidably mounted in track grooves 65 along the open side of the main body 61.

A window 66 in the cover slide 64 provides access for a laser beam for the welding operation.

The controls for the welding operation may be varied as needed for a particular welding operation. For example, the following steps and parameters were used in welding the present prototype, such as is illustrated in FIG. 1.

Three titanium subcomponents (FIGS. 15-17) are initially assembled and then welded, the subcomponents including: 1) the one-piece shell outer 21, 2) the irrigation tube 23, 3) the rear end adapter 28 (also called "female luer adapter") fitting on end of irrigation tube 23. Notably, the adapter 28 can be welded to the tube 23 ahead of welding the tube 23 to the shell outer 21 if desired. The welding creates a continuous leak-proof joint entirely around and along the tube 23 and shell 21 that is aesthetically appealing, and that is structurally robust to withstand the rigors of many cycles of surgery, cleaning, and rough handling. Notably, the illustrated welding process did not utilize a weld wire filler to overcome poor fit-up or joint design.

The illustrated welding process is somewhat complex and has many interrelated components to facilitate a high-quality, excellent-appearance weld. However, generally stated:

a. The actual weld parameters are controlled within the part run program. The program has several parameter changes to address specific challenges in target areas on the part. The "recipes" within the program include changes in Feed rates, Pulse Frequency (Hz), Energy (Joules), Pulse Duration (ms), and Energy Ramping (upslope/downslope). The energy levels vary from 2.5 Js for the "Butterfly seal" to 0.95 is in the delicate nosecone area. A person of ordinary skill in welding of titanium and in laser welding would know how to optimize those parameters, such that a detailed discussion of the parameters is not required in this disclosure.

b. Presenting the assembled part for weld is done utilizing a high performance, high precision three-jaw chuck with specially designed jaws (FIG. 15) and gas chamber (FIGS. 16-17) that allow a proper angle of presentation of the laser beam to the part for a completed one operation weld. This jaw-fixture and gas chamber allows for angle of approach to exceed 65 degrees.

c. Removing oxygen from the welding environment is critical for successful titanium welding, because Oxygen absorbed into the weld creates structural defects, reduces strength, and creates visual imperfections. The illustrated "Gas Chamber" (see FIGS. 16-17) enhances the introduction of shielding gas to the weld zone while purging the oxygen from the work envelope surrounding the part, yet does so in a manner minimizing the amount of purging gas required. The illustrated arrangement of FIGS. 16-17 is sometimes referred to as a "glove box" welding system, and is part-specific and is generally designed to reduce the costs of wasted gas while improving processing throughput.

d. Post processing of weld is an important component of the processing. While heat treating of titanium is generally known, we have incorporated a stress relieving process with good temperature/time control in order to maintain the tolerances required for subsequent processing and ultimately the finished product. The present process is believed to be new and unobvious, since it is not presently specified in known processes for forming parts similar to the present tubular shells 21, yet it yields a superior finished product, which is contrary to conventional thinking when using welding, particularly when welding without adding additional welding material such as from a welding wire.

Figure 18:
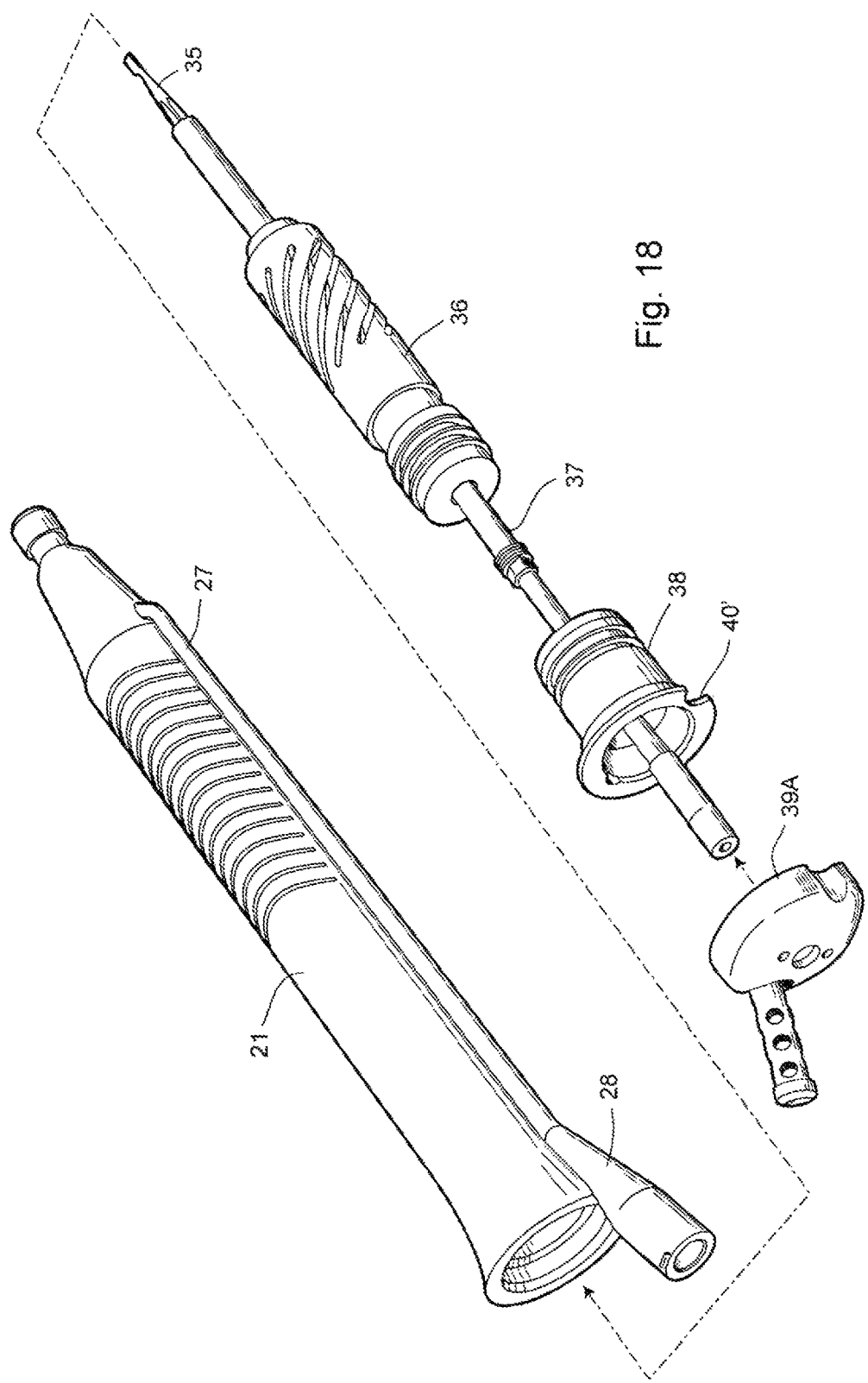

To assemble the apparatus 20 (FIG. 15), FIG. 18 illustrates the internal subassembly (i.e. the tip 35, horn 36, shaft 37, and plug 38 and including electrical wires operably connected to the horn 36) are positioned inside the external subassembly (i.e. the fully-formed outer shell 21 with irrigation tube 23 and adapter 28), and then friction-fit the tail end cap 39A (FIG. 18) on a tail end of the outer shell 21 (with the wires extending through the wiring port in the end cap 39A), thus holding the assembly together. Thereafter, as shown in FIG. 19, the adapter 28 is connected to the irrigation source/path (i.e. fluid going into the eye to equalize pressure), the tail of the interior subassembly (i.e. the tail of the multi-diameter shaft 37, which protrudes through the end cap 39A) is connected to the aspiration/fluid-debris-removal path (i.e. fluid leaving the eye that is sucked out along with organic material such as a lens and cataract), and electronic/sonic/handset wiring/tubing controls are connected the equipment system control (electronics and utilities) (or otherwise connected as required by the equipment system manufacturer).

It is to be understood that variations and modifications can be made on the aforementioned structure without departing from the concepts of the present invention, and further it is to be understood that such concepts are intended to be covered by the following claims unless these claims by their language expressly state otherwise.

The embodiments of the invention in which an exclusive property or privilege is claimed are defined as follows:

1. A subassembly for an ophthalmic surgical instrument comprising:
   a multi-diameter shaft;
   a horn fixedly threaded into the shaft and that is constructed to provide sonic vibration energy to an end opposite the shaft;
   a surgical tip for ophthalmic surgery including a tip end at one end and a threaded end threadably engaging the horn opposite the shaft, the tip end defining a face direction; and
   a plug on the shaft and having a flange with an angle-locating feature; and
   weld material holding the plug on the shaft in a selected angular and longitudinal position with the angle-locating feature having a predetermined angular clocked relation to the face direction of the tip end.

2. The subassembly of claim 1, wherein the angle-locating feature is a recess in an annular flange on the plug.

3. An ophthalmic surgical instrument comprising an outer subassembly including a tubular shell and an irrigation tube attached to a side of the shell, and including an internal subassembly comprising:
   a multi-diameter shaft;
   a horn fixedly threaded into the shaft and that is constructed to provide sonic vibration energy to an end opposite the shaft;
   a surgical tip for ophthalmic surgery including a tip end at one end and a threaded end threadably engaging the horn opposite the shaft, the tip end defining a face direction;
   a plug on the shaft and having a flange with an angle-locating feature comprising a recess in an angular flange on the plug;
   weld material holding the plug on the shaft in a selected angular and longitudinal position with the angle-locating feature having a predetermined angular clocked relation to the face direction of the tip end; and
   wherein the internal subassembly is assembled into the outer subassembly with the recess engaging the irrigation tube on the annular flange of the plug, thus causing the tip end to be in a desired angular clocked position relative to the irrigation tube on the shell.

4. An ophthalmic surgical instrument comprising a combination including:
   a tubular shell having a tip end portion and a tail end portion, and further having a channel extending from a hole into the tubular shell near the tip end portion and extending to the tail end portion; and
   an irrigation tube configured to matably engage the channel with a forward end shaped to fit into the hole and with a rear end extending at least to the tall end portion;
   the channel having a narrowed region with a protruding portion shaped to facilitate initiation of a laser welding process by providing abutting contact between the protruding portion of the tubular shell and irrigation tube that in turn provides access and point-focused heating from a laser beam welding operation, thereby facilitating heating and flowing of the material from the tubular shell into welded bonding contact with the irrigation tube with minimized physical and aesthetic defects and imperfections, yet without addition of separate welding material.

5. The instrument of claim 4, wherein the narrowed region includes deformed material of the shell that is deformed and pinched inwardly.

6. The instrument of claim 4, wherein:
   the protruding portion comprises a ridge.

7. The instrument of claim 4, wherein:
   the narrowed region is located closer to the tail end portion than the tip end portion.

* * * * *